United States Patent
Broek et al.

(10) Patent No.: US 7,144,382 B2
(45) Date of Patent: Dec. 5, 2006

(54) DEVICE FOR TREATING A FLUID-LIKE SAMPLE SUCH AS A WHOLE BLOOD, WITH TREATMENT FLUID, USE OF SUCH A DEVICE AND KIT CONTAINING SUCH A DEVICE

(75) Inventors: Arjan Jacob Broek, Delft (NL); Max van den Berg, Woerden (NL); Felix Wilhelmus Marie de Rooij, Gouda (NL)

(73) Assignee: Best Quality B.V., Woerden (NL)

( * ) Notice: Subject to any disclaimer, the term of this patent is extended or adjusted under 35 U.S.C. 154(b) by 272 days.

(21) Appl. No.: 10/476,598

(22) PCT Filed: Nov. 19, 2001

(86) PCT No.: PCT/NL01/00836

§ 371 (c)(1),
(2), (4) Date: Oct. 31, 2003

(87) PCT Pub. No.: WO02/40993

PCT Pub. Date: May 23, 2002

(65) Prior Publication Data

US 2004/0133146 A1   Jul. 8, 2004

(30) Foreign Application Priority Data

Nov. 17, 2000 (NL) .................................. 1016646

(51) Int. Cl.
- *A61M 37/00* (2006.01)
- *A31M 5/315* (2006.01)
- *A31M 5/178* (2006.01)
- *A31M 1/36* (2006.01)
- *A61N 1/30* (2006.01)

(52) U.S. Cl. .................... 604/6.09; 604/4.01; 604/183; 604/231; 604/232; 604/19; 604/6.15; 422/44

(58) Field of Classification Search ............... 604/4.01, 604/5.01, 6.04, 6.07, 6.09, 6.15, 416, 236–238, 604/246, 249, 181, 183, 6.12, 231, 232.218, 604/221, 89, 226, 19; 206/363–366
See application file for complete search history.

(56) References Cited

U.S. PATENT DOCUMENTS

| | | | | |
|---|---|---|---|---|
| 1,456,469 A | * | 5/1923 | Schwidetzky | 604/183 |
| 2,062,285 A | * | 12/1936 | Bergman | 417/437 |
| 4,453,927 A | * | 6/1984 | Sinko | 604/513 |
| 4,640,297 A | * | 2/1987 | Bates | 600/578 |
| 5,484,406 A | * | 1/1996 | Wong et al. | 604/87 |
| 5,971,953 A | * | 10/1999 | Bachynsky | 604/90 |

FOREIGN PATENT DOCUMENTS

| | | |
|---|---|---|
| EP | 0 412 225 A1 | 2/1991 |
| EP | 0 724 145 A2 | 7/1996 |
| WO | WO 97/29369 | 8/1997 |

* cited by examiner

*Primary Examiner*—Tatyana Zalukaeva
*Assistant Examiner*—Leslie R. Deak
(74) *Attorney, Agent, or Firm*—The Webb Law Firm

(57) ABSTRACT

A device for treating a fluid-like sample, in particular whole blood, with treatment fluid. The device comprises a tubular container with a first piston and a second piston, with a piston gap between them in which the treatment fluid is located in the initial position. The device further comprises an inlet port to which a capillary can be connected and an outlet port to which a filter can be connected. Furthermore, the device comprises a tubular container so that when the plunger is pushed in the first piston, the first piston moves away from the second piston in order to draw in sample from the inlet port, the two pistons are then moved jointly away from the inlet port to in front of the outlet port, after which the second piston is pushed towards the first piston in order to drive out the mixture of sample and treatment fluid, via the outlet port, through the filter

17 Claims, 4 Drawing Sheets

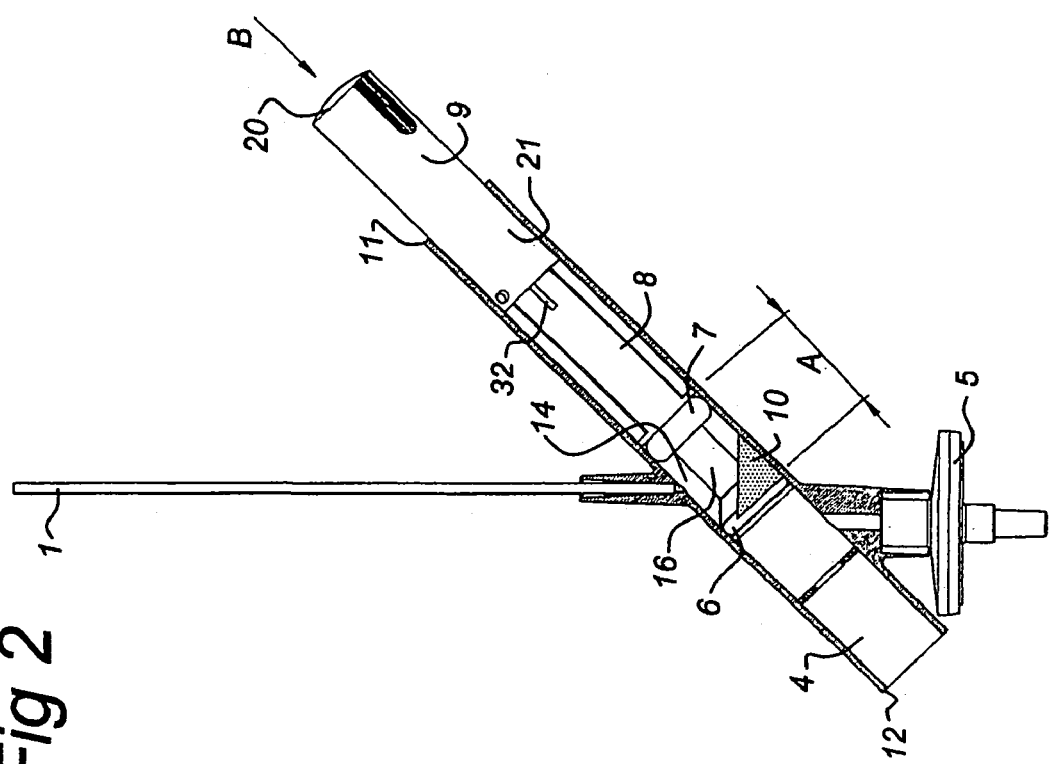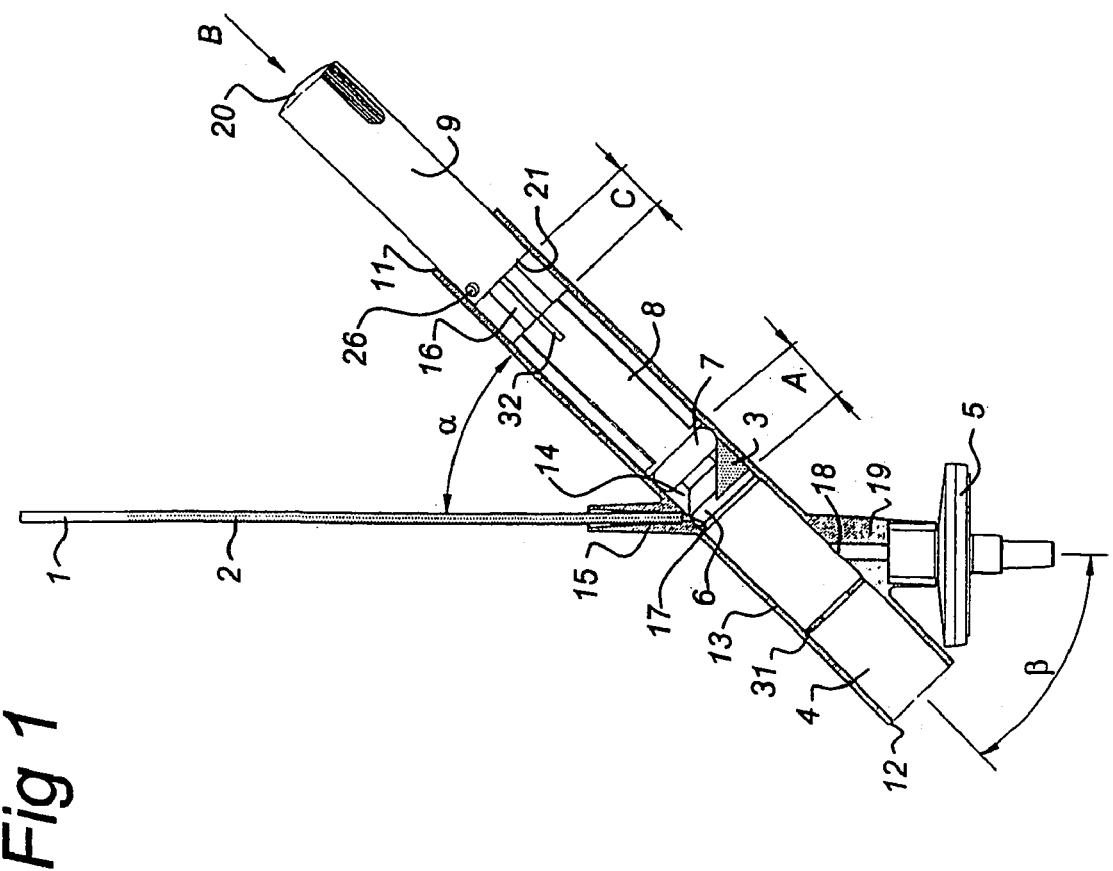

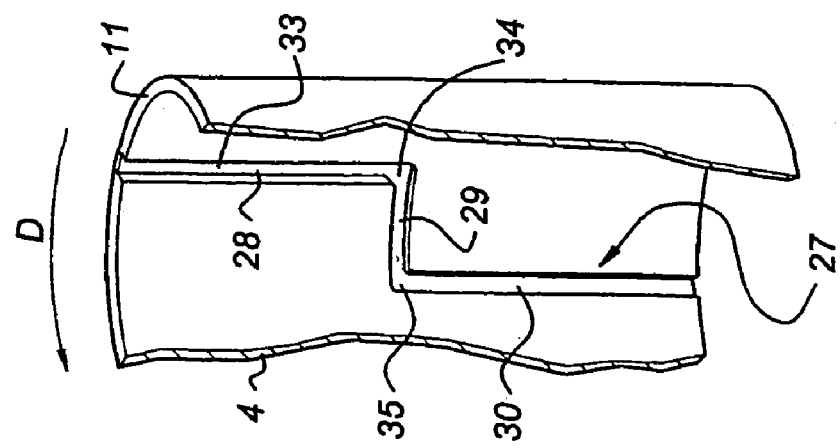
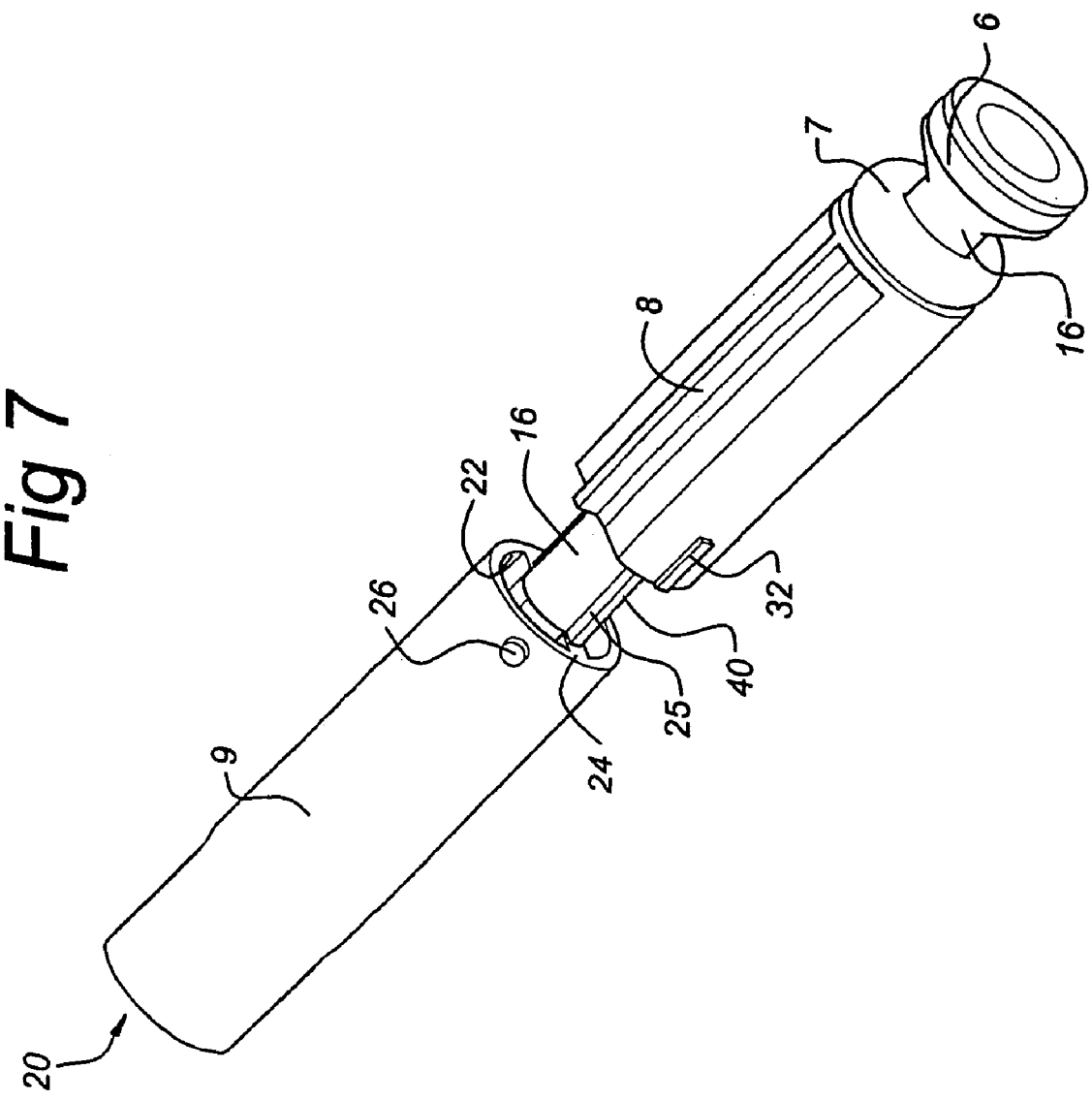

DEVICE FOR TREATING A FLUID-LIKE SAMPLE SUCH AS A WHOLE BLOOD, WITH TREATMENT FLUID, USE OF SUCH A DEVICE AND KIT CONTAINING SUCH A DEVICE

The present invention relates to a device for treating a fluid-like sample, in particular a body fluid, such as whole blood, with treatment fluid. More particularly, the present invention relates to a device for carrying out the method for the treatment of whole blood as disclosed in WO 97/29369.

In medical diagnosis the separation of plasma from whole blood is exceptionally important for analysing constituents dissolved in blood. Such analyses frequently take place with the aid of rapid diagnostic kits. Rapid diagnostic kits are, for example, supports which contain a separation matrix for separating plasma from whole blood and a test reagent. In this case a drop of whole blood is applied to the support, clear plasma passing through the separation matrix and the blood particles, such as erythrocytes and leukocytes, remaining behind in the matrix. The plasma then reacts with the test reagent, giving rise to a change in colour which is then assessed visually or spectrophotometrically. A disadvantage of these rapid diagnostic kits is that haemolysis of erythrocytes can occur, haemoglobin being entrained with the plasma and therefore being able to interfere in the colour reaction.

The abovementioned problems do not arise in the case of rapid diagnostic kits onto which plasma that does not contain haemolysis products is applied, instead of whole blood. In this case plasma first has to be separated off from the whole blood. For this purpose, WO 97/29369, which has been cited, provides a method and device for carrying this out.

In accordance with WO 97/29369 a syringe is used for mixing whole blood, anticoagulant and a diluent. With this procedure, the whole blood is taken up in the syringe by creating a vacuum in the interior of the syringe and then piercing a sealing cap provided on the nozzle of the syringe, using a needle or capillary. The whole blood is then mixed with the diluent and the anticoagulant by moving the syringe to and fro or shaking it. After removing the sealing cap a filter is fitted on the nozzle and the mixture is driven out of the syringe via the filter. The blood particles are retained in the filter, this being a filter containing glass fibres, and the (clear) blood plasma passes through, which plasma can then be used in a diagnostic test. Although the method and device from WO 97/29369, function well, the device used is capable of improvement, in particular as far as the ease of use is concerned.

The aim of the present invention is to provide a device for treating a fluid-like sample, in particular a body fluid, such as whole blood, with treatment fluid, which device can, in particular, be handled easily in use and with as few operations as possible.

Said aim is achieved according to the invention by a device for treating a fluid-like sample, in particular a body fluid such as blood, with treatment fluid, wherein the device comprises:
- a tubular container with a tube wall extending in the longitudinal direction from an upstream end of the tube to a downstream end of the tube;
- a first piston that is fitted in the tubular container and can be moved in the longitudinal direction thereof;
- a second piston that is fitted in the tubular container upstream of the first piston and can be moved in the longitudinal direction thereof;
- a piston gap that is located between the first and the second piston and is delimited by the first piston, the second piston and the section of the tube wall extending between them;
- a treatment fluid provided in the piston gap;
- an inlet port that is provided on the tube wall and has an inlet opening emerging into the tubular container, for feeding in the sample;
- an outlet port that is provided on the tube wall and has an outlet opening, downstream of the inlet opening, emerging into the tubular container, for discharging the sample treated with treatment fluid;
- a plunger that can be moved in the longitudinal direction of the tubular container; and
- coupling means which couple the first piston, the second piston, the plunger and the tubular container to one another in such a way that by moving the plunger in a single direction running parallel to the tubular container the first and the second piston move in the downstream direction from an initial position, via a first intermediate state and a second intermediate state, into an end position, the volume of the piston gap increasing between the initial position and the first intermediate state, remaining the same between the first and second intermediate state and decreasing between the second intermediate state and the end position;

the inlet opening being located in a section of the tube wall that during the stage between the initial position and the first intermediate state, or at least during part of this stage, forms part of the boundary of the piston gap, and the outlet opening being located in a section of the tube wall that during the stage between the second intermediate state and the end position, or at least during part of this stage, forms part of the boundary of the piston gap.

In this application the terms upstream and downstream relate to the direction of movement of the first and second pistons. In this context the direction of movement of the first and second pistons is considered to be the direction of flow.

By providing a separate inlet port and outlet port, interim operations with regard to removing the sample feed connection, such as a capillary, from a common port and then connecting a mixture treatment system, such as a filter, thereto are superfluous. It is possible in advance fully to prepare the device for use and to make the necessary connection to the inlet port and outlet port, and for single operation of the device then to suffice for moving the plunger. The treatment fluid is already provided in the device in advance, optionally in the factory, specifically between the first and the second piston. By, in a first stage, when going from the initial position to the first intermediate state, moving the first piston away from the second piston and thus increasing the volume of the piston gap, a vacuum is produced which, if the inlet port opens into the piston gap during this first stage, and possibly from as early as the initial position, provides for suction of the sample via the inlet opening. It is thus no longer necessary to provide a vacuum in advance, in the factory, which demands the necessary technical effort if this vacuum has to be maintained for a sufficiently long period for storage purposes. When the sample has been drawn into the piston gap the first and the second piston move jointly in the second stage, during which the device is brought from the first intermediate state into the second intermediate state, so that the connection between the piston gap and the inlet port is broken. During this second stage the first and the second piston can move at the same speed, in which case the volume of the piston gap will then remain essentially the same, but they can optionally also move at different speeds, in which case the volume then increases or decreases depending on the difference in speed. In a third stage, that involves bringing the device from the second intermediate state into the end position, the volume of the piston gap is reduced and an overpressure is thus built up. This overpressure ensures that the mixture of sample and treatment fluid is driven out of the tubular container when the outlet opening emerges into the piston gap during this third stage and optionally during the entire third stage. As will be clear to an average person skilled in the art, this progression in movement of the first and the second piston can be achieved by moving a single plunger in a single direction parallel to the tubular container. This movement can be achieved by pushing or pulling the plunger. In general, pushing the plunger will be preferred. In order to translate movement of the plunger into the desired movement of the first and the second piston, coupling means will have to be provided between the plunger and the first and the second piston and also the tubular container, which coupling means can be constructed in a wide variety of ways by a person skilled in the art. It is, for example, conceivable to use a pull rod extending through the tubular container to exert a pulling force on the first and the second piston as such in order to move these pistons. Since it is usually less easy to regulate a pulling force with high accuracy, the pulling force on the pull rod could be applied by providing a plunger, extending in the direction opposed to the pulling direction, in the form of a push sleeve around the tubular container, which push sleeve can then be moved by pressing it over the tubular container along the outside, so as then to pull the pull rod coupled thereto out of the tubular container and to provide the first and the second piston with the desired progression in movement. This desired progression in movement can easily be achieved by a person skilled in the art by providing the requisite ridge/ groove guide systems in a suitable manner, for example more or less a mirror image version of the particular embodiment explained in more detail below with reference to the figures.

In order to be able easily to obtain a sample suitable for feeding to the device according to the invention, it is advantageous according to the invention if the device also contains a capillary, where the capillary can be connected to the inlet port, preferably one end of the capillary being inserted therein in a manner that produces a seal. A fluid-like sample can be taken easily using such a capillary by bringing one end of this capillary into contact with the fluid-like sample, after which the fluid-like sample will be drawn into the capillary automatically as a consequence of the capillary action. After one end of the capillary has then been inserted into the inlet port in a manner that produces a seal and suction is created by moving the first and the second piston apart, the sample can then be fed into the piston gap.

Especially with a view to the treatment of blood samples, in particular, whole blood samples, it is advantageous according to the invention if the capillary contains an anticoagulant, such as heparin. If an anticoagulant is used, the capillary can be coated with this on the inside.

According to the invention the treatment fluid can be of diverse nature. In the case of blood samples, it will be possible for the treatment fluid to comprise, inter alia, a diluent and/or a buffer solution, such as a phosphate buffer. It will, in particular, be possible to match the treatment fluid to the diagnostic test to be carried out, or the treatment fluid may be required for the diagnostic test to be carried out. A phosphate buffer that contains 0.1% (m/m) sodium azide and has a pH of approximately 7.2 may be mentioned as an example of a phosphate buffer. The treatment fluid, such as a diluent, can also contain one or more customary surfactants, preferably non-ionic surfactants.

Especially with a view to separating off certain constituents from the mixture of the sample and the treatment fluid in order to make a specific filtrate available, it is advantageous if the device according to the invention also contains a filter for filtering the sample treated with treatment fluid. This can be, for example, a filter containing glass fibres. If a mixture of treatment fluid and a sample of whole blood is fed through such a filter, such as a filter containing glass fibres, the residual filtrate will thus then be plasma from which blood particles, such as erydirocytes and leukocytes, have been removed and is thus able to provide a more reliable result in diagnostic tests to be carried out with plasma.

Although the filter could be installed in the tubular container upstream of the outlet port, it is preferable according to the invention if the filter is connected or can be connected to the outlet port.

Although it is conceivable that the so-called plunger runs over the tubular container completely on the outside and is provided with carrier ridges or the like which protrude into the tubular container and engage on the first and/or second piston, it is preferable from the standpoint of engineering design if the plunger can be moved in the interior of the container and one end of it protrudes from the tubular container, at least in the initial position. If the plunger is a pull rod, said end will still protrude from the tubular container and in the end position will even protrude further. If the plunger is a push rod, it is then conceivable that the end that protrudes from the tubular container in the initial position is entirely or just inside the tubular container in the end position. Preferably this end will then otherwise be just completely inside the tubular container, so that the plunger cannot be pulled outwards, or at least can be pulled outwards only with great difficulty. This counteracts the risk of infection and reuse of the device according to the invention. In the case of a pusher, the plunger would thus, at least in the initial position, protrude from the upstream end of the tubular container.

One advantage of a plunger that is at least partially accommodated in the tubular container is that the plunger thus has a natural guide, that is to say the tubular container.

In order to be able to move the first piston, that is located downstream of the plunger beyond the second piston, by pushing in the plunger, it is preferable according to the invention if the first piston is arranged on a first piston stem, the first piston stem protruding, in a sealing manner that allows movement, through an opening made in the second piston and extends as far as or into the plunger.

Not carrying along the second piston in the first stage and carrying along the second piston in the second stage when the plunger is pushed in can be achieved in a simple. manner according to the invention if, in the initial position, that end of the plunger that faces downstream is, a distance away from the second piston, or has a second piston stem provided thereon, such that when the plunger is pushed in from the initial position the first piston moves away in the downstream direction from the second piston, that is preferably stationary, in order to cause the volume of the piston gap to increase until the downstream end of the plunger comes into contact with the second piston or the second piston stem on reaching the first intermediate state, and when the plunger is pushed in further from the first intermediate state the first piston and second piston move jointly in the downstream direction, at least as far as the second intermediate state.

In order to be able to allow the second piston to move towards the first piston in the third stage to reduce the volume of the piston gap, it is advantageous according to the invention if the plunger and/or first piston stem are provided with stop means that can be disengaged from a stop position into a free position, if, in the stop position, the plunger, when it is pushed in, also pushes in the first piston stem and if, in a free position, the plunger, when it is pushed in, does not also push in the piston stem or at least also pushes it in to a lesser extent than the plunger itself is pushed in. As will be clear to an average person skilled in the art without having to think about it too much, non-releasable stop means of this type can be implemented in numerous ways. Thus, for example, it is conceivable that, in order to be carried along by the plunger, the first piston stem bears on a bearing surface that breaks off when the pressure on the plunger is sufficiently high. This break-off bearing surface will then break off when the first piston, and thus also the first piston stem, is held back by, for example, an end stop. With a view to high functional reliability, it is preferable according to the invention to select a different embodiment, wherein the stop means have, on one side, a ridge face made on the first piston stem or on the plunger and have, on the other side, an accommodating space made in the plunger or, respectively, in the piston stem and extending in the longitudinal direction, wherein in the stop position the ridge face is located outside the accommodating space and is in contact with a stop or bearing surface made on the plunger or, respectively, the piston stem, and wherein in the free position the ridge face can be accommodated in the accommodating space in order to cause the plunger to move closer to the first piston when it is pushed in further. Bringing from the stop position into the free position can then be effected by turning the plunger through a suitable angle. For the purposes of reliability, this suitable angle can optionally be set by providing angle stops on either side of the ridge.

With a view to reliable functioning of the device according to the invention it is advantageous if the first piston stem, on the one hand, and the second piston and/or second piston stem, on the other hand, are incapable of turning relative to one another and are also incapable of turning with respect to the tubular container. The inability of the first piston stem to turn relative to the second piston and/or second piston stem can be achieved in a simple manner by making the first piston stem rectangular or triangular, for example, and making the passage formed in the second piston for the first piston stem and/or the passage formed in the second piston stem for the first piston stem of corresponding shape. Constructing the first piston stem and second piston and/or second piston stem such that they are incapable of turning with respect to the tubular container can be achieved in a simple manner by providing the first piston stem or the second piston stem (or optionally the second piston) with one or more ridges which are guided through a longitudinal groove running in the inside of the tubular container. However, as is known to an average person skilled in the art, making components incapable of turning can also be achieved in other ways.

With a view to reliable functioning it is furthermore advantageous according to the invention if the tangential orientation of the plunger with respect to the tubular container—that is to say the freedom of rotation of the plunger about a longitudinal axis with respect to the tubular container—is determined by a guide pin/groove combination provided on the outside of the plunger or, respectively, on the inside wall of the tubular container. The guide groove in the inside wall of the tubular container can be given any desired shape, as a consequence of which the plunger can be subjected to rotation when it is pushed in, depending on the shape of the guide groove. In this way it is possible to initiate or indeed to terminate various stages of movement by pushing in the plunger. The transition from the second stage to the third stage is thus achieved in an advantageous manner with the device according to the invention if the guide groove has a peripheral section extending in the tangential direction, preferably essentially exclusively tangential direction, at the level of the second intermediate state, in order to turn the plunger with respect to the first piston stem in such a way that the ridge comes into alignment with the longitudinal groove. The section of the periphery extending in the tangential direction can run in the form of a helix and thus ensure gradual automatic transition from the second to the third stage when the plunger is pushed in further. However, according to the invention it is preferable if the section of the periphery extending in the tangential direction extends exclusively in the tangential direction. In this way it is no longer possible to continue the pushing-in movement uninterrupted from the second to the third stage. The pushing-in movement will have to be interrupted in order to turn the plunger through a desired angle. This has the advantage that a pause then necessarily has to be introduced before driving the mixture out via the outlet port. This pause can then be utilised to subject the tubular container to a shaking movement. This prevents an inadequately mixed mixture from being driven out via the outlet port during the third stage. Specifically, there is an automatic reminder to mix, because the pushing-in movement is interrupted at a fixed point before the expulsion stage.

In order to be able reliably to ensure that the volume of the piston gap is reduced in the final stage, it is preferable according to the invention if an end stop with which the first piston comes into contact during or from the second intermediate state is provided in the tubular container. This end stop will be provided downstream of the outlet opening a distance away that is greater than or equal to the thickness of the first piston, such that the first piston exposes the outlet opening.

So that it is ensured that the entire mixture of treatment fluid and sample is driven out in the third stage, it is preferable according to the invention if the piston gap contains a gas, such as air, in addition to the treatment fluid in the initial position and if the volume of the piston gap in the initial position is greater than the volume of the piston gap in the end position to such an extent that it is ensured that all of the sample treated with the treatment fluid is driven out of the tubular container, preferably forced through the filter, in the end position. This prevents the need for excess volume, which must be avoided as far as possible in the case of, for example, blood samples.

With a view to the ease of use, it is preferable according to the invention if the inlet port and outlet port are provided on opposite sides of the tube wall, run essentially parallel to one another and, with respect to the longitudinal direction of the tubular container, are in a tilted sloping position, at preferably 30° to 60°, such as approximately 45°, to one of the ends of the tube, preferably towards the upstream end of the tube and the downstream end of the tube, respectively. In this way it is possible to hold the device during use angled obliquely downwards in the direction of flow, with the outlet port and inlet port both essentially vertical. The fluid issuing from the outlet port or the filter optionally mounted thereon can then be dispensed directly, for example dropwise, to a diagnostic test device.

According to a further aspect the present invention relates to the use of a device according to the invention for the treatment of a sample of a body fluid, such as blood.

According to yet a further aspect the invention relates to the use of a device according to the invention for separating plasma from a blood sample of whole blood.

According to yet a further aspect the invention relates to a kit for separating plasma from whole blood and carrying out a diagnostic test on the plasma, comprising:

a device according to the invention;
a capillary, that preferably contains anticoagulant;
a filter, preferably a filter containing glass fibres; and
at least one diagnostic test device.

As far as a diagnostic test device is concerned, consideration can be given, for example, to cardboard or paper plates with a test reagent thereon that is able to give a specific reaction on contact with plasma, depending on the constituents contained in the plasma.

The present invention will be explained in more detail below with reference to an illustrative embodiment shown in the drawing. In the drawing:

FIG. 1 shows a diagrammatic, partially exposed, side view of a device according to the invention in the initial position;

FIG. 2 shows a view corresponding to FIG. 1, but now in the first intermediate position;

FIG. 7 shows, diagrammatically and in perspective, part of the interior of the device according to the invention; and FIG. 8 shows, diagrammatically, as a detail and in longitudinal section, an additional angular section of the tubular container.

Figure 3:
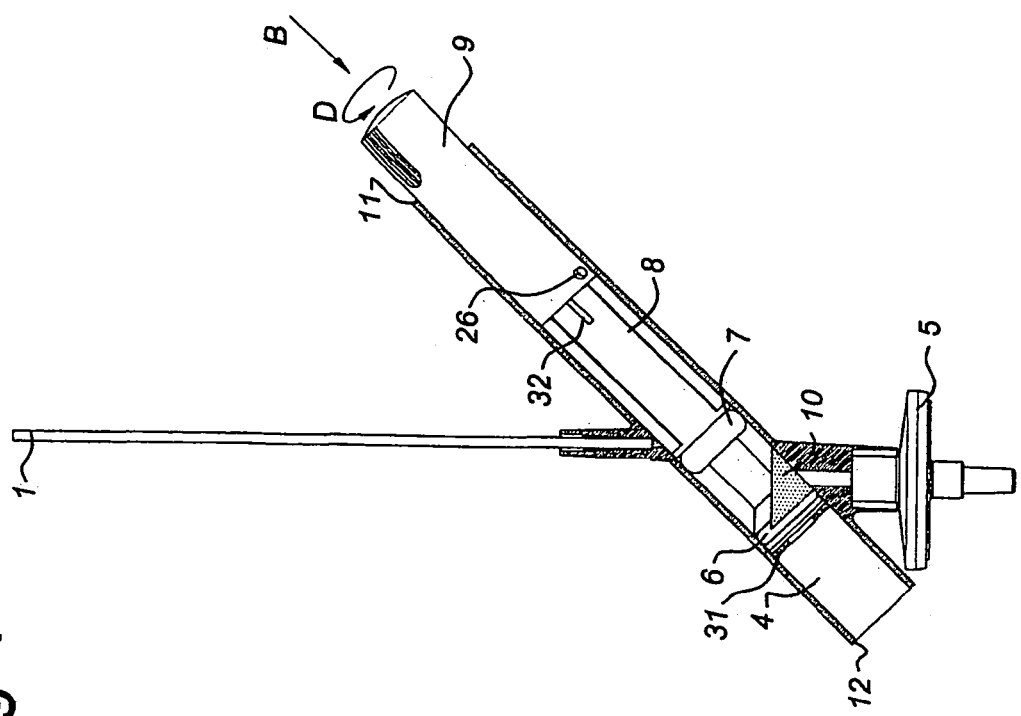
FIG. 3 shows a view corresponding to that in FIGS. 1 and 2, but now during the transition from the first to the second intermediate state.

Before discussing the figures in more detail it is pointed out, in particular with regard to FIGS. 1–5, that for the sake of clarity all reference numerals and symbols have not been indicated in all these figures. However, it will be clear that the reference numerals and symbols can be entered in all these figures since the device is the same, shown in various positions.

With reference to the figures, a preferred embodiment of a device according to the invention comprises:

a tubular container 4 with an upstream tube end 11, a downstream tube end 12 and a tube wall 13 extending between them; a first piston 6 that engages all round in a manner that produces a seal with the interior of the tube wall 13 and can be moved in the longitudinal direction of the tubular container and that is fixed to the bottom end of a first piston stem 16; a second piston 7 that likewise seals all round on the interior wall of the tube wall 13 and can be moved in the longitudinal direction of the tubular container 4 and seals against the first piston stem; a second piston stem 8 in contact with the second piston 7 or firmly joined thereto; a piston gap 14 located between the first piston 6 and second piston 7 and delimited by the pistons 6, 7 and the section A of the tube wall extending between them, through which piston gap 14 part of the first piston stem 16 extends; in the initial position shown in FIG. 1, a treatment fluid 3 that is present in the piston gap 14; an inlet port 15 with an inlet opening 17 emerging into the interior of the tubular container 4; a capillary 1, one end of which can be inserted, or has been inserted as is shown, into the inlet port 15 in a manner that produces a seal; an outlet port 19 that is in communication with the interior of the tubular container 4 via an outlet opening 18; and a filter 5, containing glass fibres as filter material, that is connected to the outlet port 19 by means of a Luer connector; and a plunger 9 with an upstream end 20 and a downstream end 21.

In the initial position shown in FIG. 1, capillary 1 filled with a sample of whole blood 2 has been inserted in the inlet port 15 to form a tight-fitting seal therewith. The pistons 6 and 7 are still in the initial position, in which they have a gap A between them that defines a relatively small piston gap 14. In the initial position a treatment fluid 3, for example a phosphate buffer, is provided in the piston gap 14. In this case this treatment fluid 3 can have been provided in the piston gap 14 in the factory, but it is also conceivable that the person carrying out the test introduces this treatment fluid 3 into the piston gap 14 him- or herself. In the initial position the first piston 6, which is the front piston in the downstream direction B, just does not close off the inlet opening 17, although it is advantageously readily conceivable that the first piston 6 does just close off the inlet opening 17 in order, for example, to prevent treatment fluid 3 from being able to flow out of the tubular container 14 via the inlet opening 17 and inlet port 15 during storage. At least a portion of the first piston stem 16 has a non-circular cross-section and a preferably external round or elliptical portion of this piston stem 16 extends through a correspondingly shaped passage in the second piston so that, in particular as a consequence of the external round or elliptical shape, it can move in a sealed manner with respect to said second piston 7, which can be constructed as a rubber-like ring. The first piston stem 16 extends as far as or into the plunger 9 (see detail FIG. 7). The first piston stem 16 is provided with two ridge faces 25 which in the initial position are in contact with the bearing surfaces 24 made on the plunger 9. The plunger 9 is provided with a guide pin 26 that is accommodated in a guided manner in a guide groove 27 made in the interior of the tube wall 13 (see detail FIG. 8). In the initial position (FIG. 1) the guide pin 26 is approximately at the level of 33 in the upper vertical section 28 of the guide groove 27. In this way it is ensured that the plunger 9 is not able to turn with respect to the tubular container 4, at least as long as the guide pin 26 is in the upper straight groove section 28. For the sake of correctness it is pointed out that FIG. 8 shows an exposed detail view, looking obliquely from a direction opposed to the directions of view in FIGS. 1–5 (that is to say from the rear of the plane of the drawing). In a manner corresponding to that for the guide pin 26 and guide groove 27, the second piston stem 8 is also provided with, in this case, two guide ridges 32 which project into guide grooves, which are not shown, made in the interior of the tube wall 13, which latter guide grooves will run precisely parallel to the longitudinal direction of the tubular container 4 if the second piston stem 8 is incapable of turning with respect to the tubular container 4. The second piston stem 8 is of hollow construction so that the first piston stem 16 can run through it. In order to make the first piston stem 16 incapable of turning, a passage section which has a shape corresponding to that of the non-circular peripheral shape of the upstream section of the first piston stem 16 will be made in the interior of the second piston stem 8. This non-circular shape is obtained by providing a round core section with two diametrically opposed ribs 40. These ribs 40 are accommodated in guiding longitudinal channels 41 made in the interior of the second piston stem. The ridge faces 25 are formed by the upstream end surfaces of the ribs 40.

If the plunger 9 is now pushed obliquely downwards from the initial position in FIG. 1 in accordance with the arrow B, this pin will push the first piston stem 16 out in front of it (after all, the ridge faces 25 formed thereon are in contact with the bearing surfaces 24 on the plunger 9) in order finally for its downstream lower end 21 to come into contact with the upper end of the second piston stem 8. Up to the point in time when the plunger 9 makes contact with the second piston stem 8, the second piston 7 will, as a consequence of its sealing, tight-fitting engagement with the inside wall of the tube wall 13, remain in place and the distance between the first piston 6 and the second piston 7 will thus increase. As a consequence of the increase in the distance between the pistons, the volume of the piston gap 14 will increase and the sample, in particular whole blood, present in the capillary 1 will be drawn out of the capillary into the piston gap 14. So as not to influence the seal between the first piston stem 16 and the second piston 7, it is preferable according to the invention if, in the first intermediate state shown in FIG. 2, the ribs 40 at most just touch the upstream side of the second piston. In practice, the ribs 40 will end some distance away from the second piston 7 in this first intermediate state.

FIG. 2 shows the so-called first intermediate position in which the plunger 9 has just come into contact with the second piston stem 8 and in which all the sample 2 present in capillary 1 has been drawn into the piston gap 14. A mixture 10 of treatment fluid 3 and sample 2 that, as is shown in FIG. 2, will have a greater fluid volume, is thus present in the piston gap 14. By way of indication of volume magnitudes, consideration can be given to 75 μl sample 2 in the capillary 1 that finally has passed completely into the piston gap 14 and to originally 135 μl treatment fluid 3 in the initial position, so that in the first intermediate state shown in FIG. 2 approximately 210 μl of mixture 10 is in the piston gap 14. In this case it will be possible for the total volume of the piston gap in the first intermediate state as shown in FIG. 2 to be approximately 1 to 1.3 ml.

From the so-called first intermediate state shown in FIG. 2 the first and the second piston move jointly further, with a constant mutual spacing, when pushing-in of the plunger 9 is continued or resumed. Via the interim intermediate state shown in FIG. 3, the so-called second intermediate state shown in FIG. 4 will finally be reached. In the interim intermediate state shown in FIG. 3 the upper, second piston 7 is in front of the inlet opening 17 of the inlet port 15, whilst the first piston 6 has just not yet reached the outlet opening 18 of the outlet port 19 or possibly is still closing this off.

Figure 4:
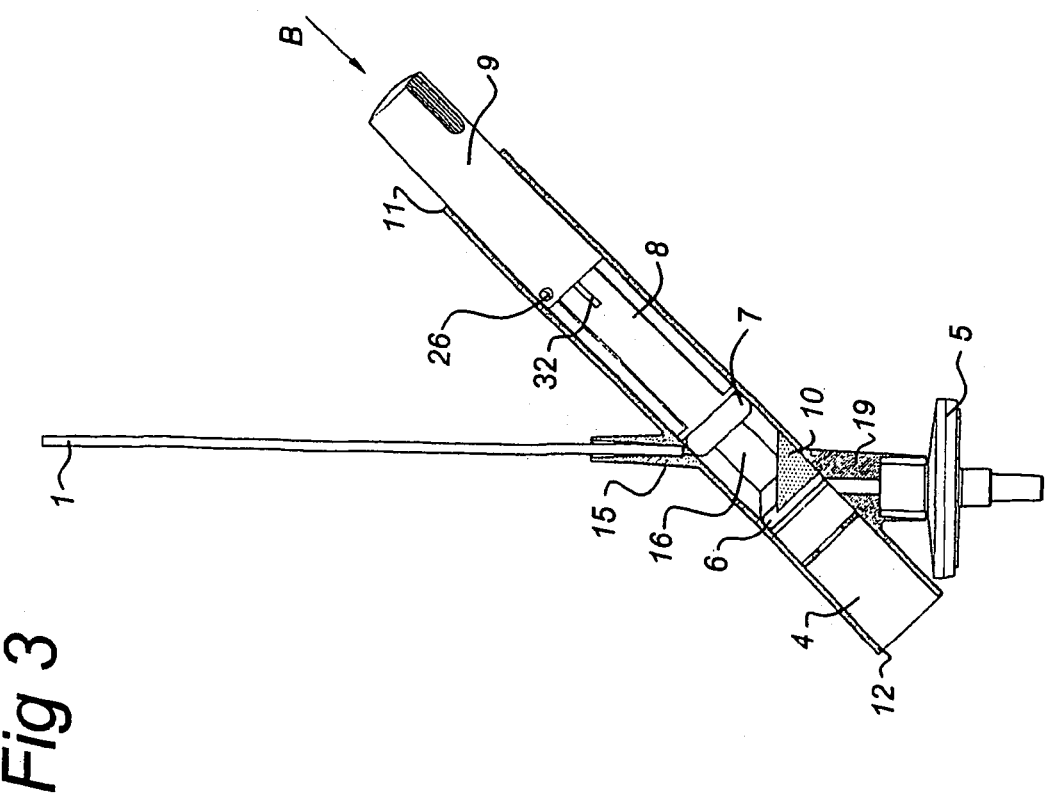
FIG. 4 shows a diagrammatic view corresponding to that in FIGS. 1–3, but now in the second intermediate state.
Figure 6:
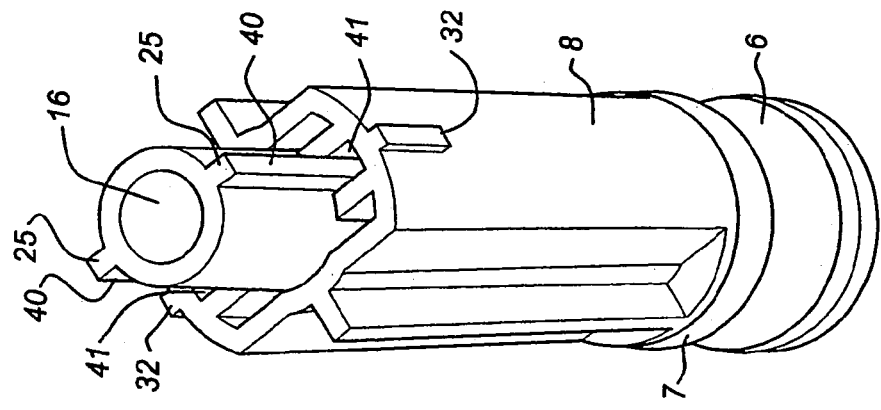
FIG. 6 shows, diagrammatically and in perspective, part of the interior of the device according to the invention.

The so-called second intermediate state shown in FIG. 4 is reached as soon as the first piston 6 comes into contact with an end stop 31 made in the interior of the tubular container 4. So as not to obtain a pressure build-up between the first piston 6 and the end stop 31, which would impede further pushing-in of the plunger 9, the annular end stop 31 is provided with a passage in the middle. However, it is pointed out that the end stop 31 can also be of different construction, for example in the form of a single ridge projecting radially inwards. Reaching the so-called second intermediate state is marked in that the guide pin 26 on the plunger 9 reaches position 34 at the bottom of the first section 28 of the guide groove 27. As will be clear, the tangential portion, or the portion running in the peripheral direction 29 of the guide groove 27 then acts as a stop to prevent the plunger 9 being pushed in further and the end stop 31 is not (yet) needed for this second intermediate state.

In this second intermediate state the first piston 6 can be in contact with the stop 31 but it can also still be some distance in front of it. The point in time when the guide pin 26 reaches the position 34 (FIG. 8) is the point in time when pushing in of the guide pin 9 is forcibly interrupted. The user of the device according to the invention is now able, without being able to forget this, to shake the device according to the invention or to subject it to a swinging movement or some other sort of shaking movement in order to mix well the mixture 10 of sample 2 and treatment fluid 3. The user will then turn the plunger 9, as is indicated by arrow D in FIGS. 4 and 8, through an angular distance of, for example, 90° in order to bring the guide pin 26 into the position indicated by 35 in FIG. 8, which position corresponds to the position of the guide pin 26 indicated in FIG. 4. As will be clear, when the plunger 9 is pushed in further the guide pin 26 will now move through the section 30 of the guide groove 27. As a result of turning the plunger 9 through the said 90° in accordance with arrow D the ribs 40 made on the second piston stem 8, or at least the ridge faces 25, will move away from the bearing surfaces 24 so as to slide into the cavity 22 in the interior of the plunger 9 when the plunger 9 is pushed in further. What is achieved in this way is that when the plunger 9 is pushed in further it moves over the first piston stem 16 and thus no longer carries the first piston stem 16 along with it.

Figure 5:
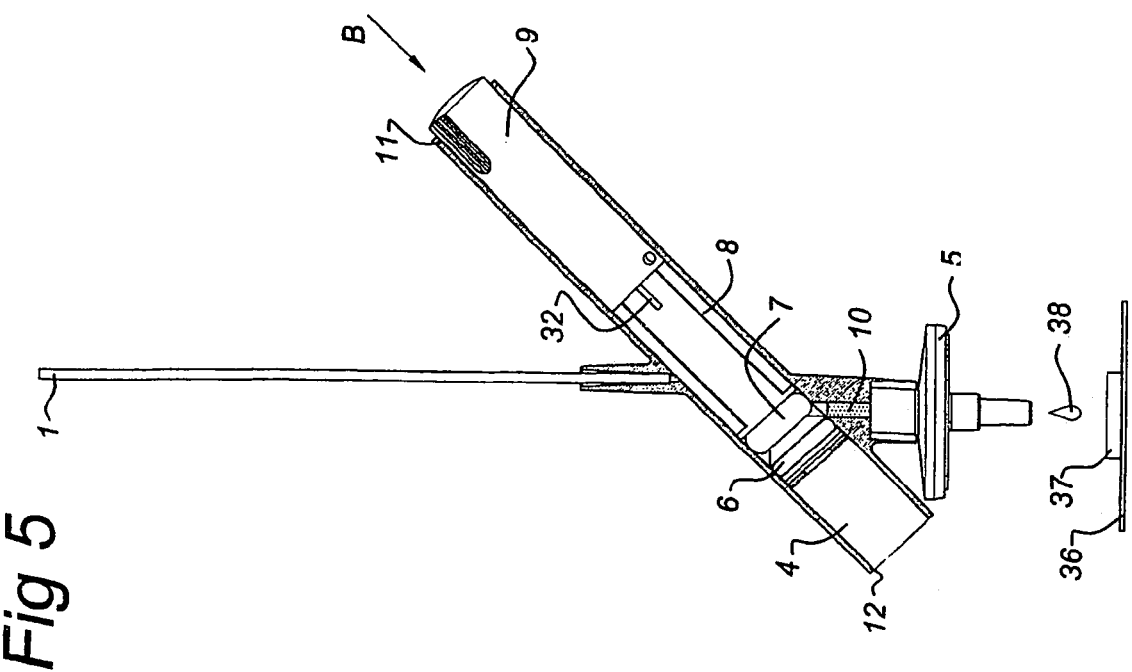
FIG. 5 shows a view corresponding to that in FIGS. 1–4, but now in the end position.

When the plunger 9 is now pushed in further with the ridge faces 25 free opposite the cavity 22 and the guide pin 26 at the start of or in the section 30 of the guide groove 27, the second piston 7 will then be able to move towards the first piston 6 in order to reduce the volume 14 between the pistons, which is delimited between the first and the second piston, and to drive out the mixture 10, until the end position shown in FIG. 5 is reached. If the first piston 6 is already in contact with the end stop 31, the pistons will immediately start to move towards one another when the plunger is pushed in further. If the first piston 6 is still some distance away from the end stop 31, the first piston 6 will initially still move forward. at the same speed as or more slowly than the second piston 7 so as to come to a stop when it comes into contact with the end stop 31. As is shown diagrammatically in FIG. 5, when mixture 10 is driven out droplets 38 thereof can be placed directly onto a diagnostic test device, consisting of, for example, a sheet 36 with a test reagent 37 thereon.

By positioning the outlet port 19 at an angle of 30 to 60°, for example approximately 45°, and preferably also positioning inlet port 15 at an angle of 30° to 60°, for example approximately 45°, the user is able to hold the device according to the invention pointing obliquely downwards in order to dispense the droplets 38 onto the underlying diagnostic test device 36, 37 with a clear view. The angles do not have to be identical. If the angle β is 45°, the angle α can very readily be zero or 135°.

The invention claimed is:

1. A device for treating a fluid-like sample, in particular a body fluid such as blood, with treatment fluid, wherein the device comprises:
    a tubular container with a tube wall extending in the longitudinal direction from an upstream end of the tube to a downstream end of the tube;
    a first piston that is fitted in the tubular container and can be moved in the longitudinal direction thereof;
    a second piston that is fitted in the tubular container upstream of the first piston and can be moved in the longitudinal direction thereof;
    a piston gap that is located between the first and the second piston and is delimited by the first piston, the second piston and the section of the tube wall extending between them;

a treatment fluid provided in the piston gap;

an inlet port that is provided on the tube wall and has an inlet opening emerging into the tubular container, for feeding in the sample;

an outlet port that is provided on the tube wall and has an outlet opening, downstream of the inlet opening, emerging into the tubular container, for discharging the sample treated with treatment fluid;

a plunger that can be moved in the longitudinal direction of the tubular container; and coupling means which couple the first piston, the second piston, the plunger and the tubular container to one another in such a way that by moving the plunger in a single direction running parallel to the tubular container the first and the second piston move in the downstream direction from an initial position, via a first intermediate state and a second intermediate state, into an end position, the volume of the piston gap increasing between the initial position and the first intermediate state, remaining the same between the first and second intermediate state and decreasing between the second intermediate state and the end position;

the inlet opening being located in a section of the tube wall that during the stage between the initial position and the first intermediate state, or at least during part of this stage, forms part of the boundary of the piston gap, and the outlet opening being located in a section of the tube wall that during the stage between the second intermediate state and the end position, or at least during part of this stage, forms part of the boundary of the piston gap wherein said device further comprises a capillary, wherein the capillary can be connected to the inlet port, and wherein the capillary contains an anticoagulant and the capillary can be inserted in the inlet port in a manner that produces a seal.

2. The device according to claim 1, wherein the interior of the capillary is coated with heparin.

3. The device according to claim 2, wherein the treatment fluid comprises a diluent and/or a buffer solution.

4. The device according to claim 3, wherein the device further comprises a filter for filtering the sample treated with treatment fluid.

5. The device according to claim 4, wherein the filter is connected to or can be connected to the outlet port, the treatment fluid is phosphate buffer, and the filter contains glass fibres.

6. The device according to claim 5, wherein the plunger can be moved in the interior of the container and one end of it protrudes from the tubular container, at least in the initial position.

7. The device according to claim 6, wherein, at least in the initial position, the plunger protrudes from the upstream end of the tubular container.

8. The device according to claim 7, wherein the first piston is arranged on a first piston stem, the first piston stem protruding, in a sealing manner that allows movement, through an opening made in the second piston and extends as far as or into the plunger.

9. The device according to claim 8, wherein in the initial position that end of the plunger that faces downstream is a distance away from the second piston, or a second piston stem provided thereon, such that when in the plunger is pushed in from the initial position the first piston moves away in the downstream direction from the second piston in order to cause the volume of the piston gap to increase until the downstream end of the plunger comes into contact with the second piston or the second piston stem on reaching the first intermediate state, and when the plunger is pushed in further from the first intermediate state the first piston and second piston move jointly in the downstream direction, at least as far as the second intermediate state.

10. The device according to claim 8, wherein the plunger and/or first piston stem are provided with stop means that can be disengaged from a stop position into a free position, wherein, in the stop position, the plunger, when it is pushed in, also pushes in the first piston stem and wherein, in a free position, the plunger, when it is pushed in, pushes the piston stem in to a lesser extent than the plunger itself is pushed in.

11. The device according to claim 10, wherein the stop means have, on one side, a ridge face made on the first piston stem or on the plunger and have, on the other side, an accommodating space made in the plunger or, respectively, in the piston stem and extending in the longitudinal direction, wherein in the stop position the ridge face is located outside the accommodating space and is in contact with the stop surface made on the plunger or, respectively, the piston stem, and wherein in the free position the ridge face can be accommodated in the accommodating space in order to cause the plunger to move closer to the first piston when it is pushed in further.

12. The device according to claim 11, wherein the first piston stem, on the one hand, and the second piston and/or second piston stem, on the other hand, are incapable of turning relative to one another and are also incapable of turning with respect to the tubular container.

13. The device according to claim 12, wherein the tangential orientation of the plunger with respect to the tubular container is determined by a guide pin/groove combination provided on the outside of the plunger or, respectively, on the inside wall of the tubular container.

14. The device according to claim 13, wherein the guide groove has a peripheral section extending in the tangential direction at the level of the second intermediate state, in order to turn the plunger with respect to the first piston stem in such a way that the ridge comes into alignment with the longitudinal groove.

15. The device according to claim 14, wherein an end stop with which the first piston comes into contact during or from the second intermediate state is provided in the tubular container and wherein the guide groove has a peripheral section extending in the essentially exclusively tangential direction.

16. The device according to claim 15, wherein the piston gap contains a gas in addition to the treatment fluid in the initial position and wherein the volume of the piston gap in the initial position is greater than the volume of the piston gap in the end position to such an extent that it is ensured that all of the sample treated with the treatment fluid is driven out of the tubular container in the end position.

17. The device according to claim 16, wherein the gas is air and further wherein the inlet port and the outlet port are provided on opposite sides of the tube wall, which inlet port and outlet port run essentially parallel to one another and, with respect to the longitudinal direction of the tubular container, are in a tilted sloping position to one of the ends of the tube.

* * * * *